United States Patent [19]
Shieh

[11] Patent Number: 6,030,781
[45] Date of Patent: Feb. 29, 2000

[54] ELECTRIC FIELD AMPLIFIED OLIGONUCLEOTIDE LIGASE ANALYSIS

[75] Inventor: Chan-Long Shieh, Paradise Valley, Ariz.

[73] Assignee: Motorola, Inc., Schaumburg, Ill.

[21] Appl. No.: 08/956,674

[22] Filed: Oct. 23, 1997

[51] Int. Cl.[7] ............................... C12Q 1/68; C12P 19/34
[52] U.S. Cl. ......................... 435/6; 435/91.2; 435/91.5; 435/91.52
[58] Field of Search ............................ 435/6, 91.1, 91.5, 435/91.52, 91.02; 536/23.1, 24.3

[56] References Cited

U.S. PATENT DOCUMENTS

| | | | |
|---|---|---|---|
| 5,434,049 | 7/1995 | Kano | 435/6 |
| 5,527,670 | 6/1996 | Stanley | 435/6 |
| 5,728,532 | 3/1998 | Ackley | 435/6 |
| 5,731,416 | 3/1998 | Garner | 530/350 |
| 5,849,486 | 12/1998 | Heller | 435/6 |
| 5,874,046 | 2/1999 | Megerle | 422/68.1 |

OTHER PUBLICATIONS

Dubiley et al (1997). Fractionation, phosphorylation, and ligation on oligonucleotide microchips to enhance sequencing by hybridization. Nucleic Acids Research 25:2259–2265, Jun. 1997.

*Primary Examiner*—Carla J. Myers
*Assistant Examiner*—Diana Johannsen
*Attorney, Agent, or Firm*—Eugene A. Parsons; William E. Koch

[57] ABSTRACT

An electric field amplified oligonucleotide ligase analysis includes combining a plurality of oligonucleotide probes carried on a support at a binding site with a solution including a target molecule, a plurality of oligonucleotide segments including a marker and ligase. A first electric field surrounding the plurality of oligonucleotide probes is generated to attract the target molecule to a first of the plurality of oligonucleotide probes to which it hybridizes. A first of the plurality of oligonucleotide segments also hybridizes with the target molecule and covalently bonds to the first oligonucleotide probe due to the presence of ligase in the solution. The target molecule is separated by generating a second electric field surrounding the plurality of oligonucleotide probes. The generation of the electric fields are alternately repeated to amplify the hybridization signal.

8 Claims, 1 Drawing Sheet

ELECTRIC FIELD AMPLIFIED OLIGONUCLEOTIDE LIGASE ANALYSIS

FIELD OF THE INVENTION

The present invention relates to molecular detection methods and more particularly to molecular detection methods which utilize ligase analysis.

BACKGROUND OF THE INVENTION

Recently, an increased effort has been directed toward the development of chips for molecular detection. In general, a molecular detection chip includes a substrate on which an array of binding sites is arranged. Each binding site (or hybridization site) has a respective molecular receptor (or probe) which binds or hybridizes with a molecule having a predetermined structure. A sample solution is applied to the molecular detection chip, and molecules in the sample bind or hybridize at one or more of the binding sites. The particular binding sites at which hybridization occurs are detected, and one or more molecular structures within the sample are subsequently deduced.

Of great interest are molecular detection chips for gene sequencing. These chips, often referred to as DNA chips, utilize an array of selective binding sites each having respective single-stranded DNA probes. A sample of single-stranded DNA fragments, referred to as target DNA, is applied to the DNA chip. The DNA fragments attach to one or more of the DNA probes by a hybridization process. By detecting which DNA probes have a DNA fragment hybridized thereto, a sequence of nucleotide bases within the DNA fragment can be determined.

Often, a sample to be tested will contain very few target molecules. Since there are few target molecules to identify, there can only be a few hybridization events which occur. Detecting a very low number of hybridization events can be extremely difficult. In effect, the signal to be detected will have very low gain and be difficult to separate from background noise. This problem has been ameliorated to some degree by the development of a process referred to as ligase analysis.

In ligase analysis, a DNA probe is immobilized on a support structure and immersed in a solution containing a segment of DNA carrying a marker, ligase and target DNA molecules. Under the proper conditions, the target DNA will hybridize with the probe and the segment of DNA carrying the marker. In the presence of ligase, the DNA probe and the segment of DNA will form a covalent bond. Since the target molecule is coupled to the DNA probe and the segment of DNA by a hydrogen bond, which is weaker than a covalent bond, the target molecule can be separated from the DNA probe and the segment of DNA without breaking the covalent bond coupling the DNA probe and the segment of DNA. This is typically accomplished by increasing the temperature of the solution. Once the target molecule is separated, the solution is again put in the proper condition for hybridization. The steps are repeated until the number of markers indicating a hybridization event is large enough to be detected over the background noise. In effect, the signal gain has been amplified by repeated hybridizations using the same target molecules.

There are many problems with ligase analysis. The proper conditions for hybridization can vary between target molecules. The time involved to process through a number of cycles is immense, as the solution must be slowly heated to a temperature sufficient to break the hydrogen bond while leaving the covalent bond intact and then allowed to cool for further hybridization. Furthermore, heat distribution becomes very important to uniformly heat and cool the solution and heat resistant ligase must be used so that viable ligase is present throughout the cycles.

It would be highly advantageous, therefore, to remedy the foregoing and other deficiencies inherent in the prior art.

Accordingly, it is an object of the present invention to provide a new and improved method and apparatus for identifying molecules.

Another object of the present invention is to provide a new and improved method for identifying molecules employing ligase analysis.

And another object of the present invention is to provide a new and improved method for ligase analysis of molecules, having greatly reduced cycle time.

Yet another object of the present invention is to provide a new and improved method for ligase analysis of molecules, without requiring heat resistant ligase.

SUMMARY OF THE INVENTION

Briefly, to achieve the desired objects of the instant invention, in accordance with a preferred embodiment thereof, provided is an electric field amplified oligonucleotide ligase analysis including providing a support having a plurality of oligonucleotide probes at a binding site thereon and a solution including a plurality of oligonucleotide segments including a marker and ligase. Target molecules are introduced into the solution and a first electric field surrounding the plurality of oligonucleotide probes is generated to attract the target molecule to a first of the plurality of oligonucleotide probes to which it hybridizes. A first of the plurality of oligonucleotide segments also hybridizes with the target molecule and covalently bonds to the first oligonucleotide probe due to the presence of ligase in the solution. The target molecule is separated from the first oligonucleotide probe and the first oligonucleotide segment by generating a second electric field surrounding the plurality of oligonucleotide probes. The first electric field surrounding the plurality of oligonucleotide probes is again generated to attract the target molecule to a second of the plurality of oligonucleotide probes to which it hybridizes, whereupon a second of the plurality of oligonucleotide segments hybridizes with the target molecule and covalently bonds to the second oligonucleotide probe due to the presence of ligase in the solution.

BRIEF DESCRIPTION OF THE DRAWINGS

The foregoing and further and more specific objects and advantages of the instant invention will become readily apparent to those skilled in the art from the following detailed description of the preferred embodiment thereof taken in conjunction with the drawings in which.

DETAILED DESCRIPTION OF A PREFERRED EMBODIMENT

Figure 1:
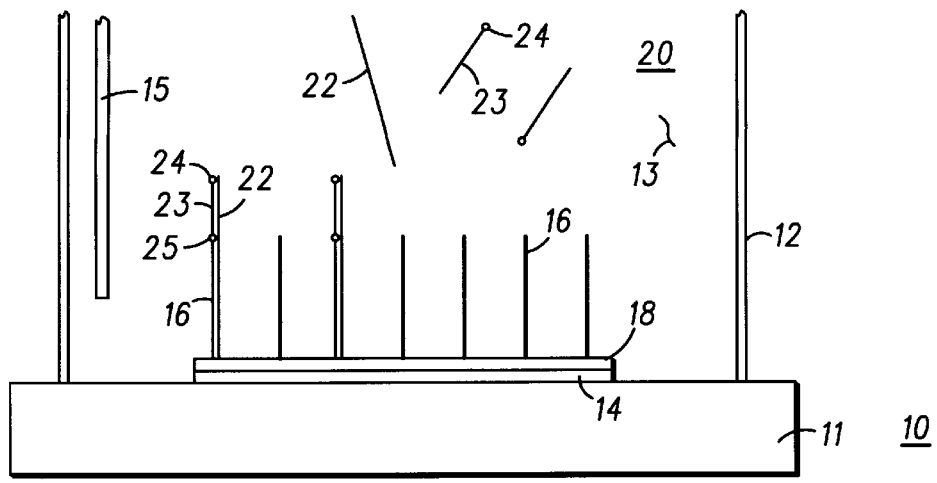
FIG. 1 is a simplified sectional side view of a molecular detection apparatus employed in the method of the present invention as it would appear during hybridization and ligation.

Turning now to the drawings in which like reference characters indicate like elements throughout the several views, attention is first directed to FIG. 1 which illustrates a molecular detection apparatus generally designated 10. Molecular detection apparatus 10 includes a support 11 and barrier 12 extending therefrom to define a volume 13. An electrode 14 is formed on support 11 defining a binding site within volume 13, and a counter electrode 15 is carried within volume 13, spaced from electrode 14. A plurality of oligonucleotide molecular receptors (probes) 16 are immobilized on electrode 14 In the preferred embodiment, oligonucleotide probes 16 are covalently bonded to the surface of electrode 14 by a polymer permeation layer 18 in a known manner. Each of molecular receptors 16 carried by electrode 14 are substantially identical.

In general, molecular receptors 16 are selected in dependence upon a type of target molecule which is to be detected. Each probe 16 includes a molecule that has a specific affinity to the target molecule to be detected. The molecule includes a chain of at least one nucleotide which hybridizes with a complementary chain of at least one nucleotide included in the target molecule. In the present invention, probes 16 can include DNA strands or preferably include a peptide nucleic acid (PNA) composed of nucleotide bases carried by a peptide backbone for detecting a corresponding, complementary base sequence in the target molecule.

PNA binds to single stranded DNA the same as complimentary DNA, only with more affinity and greater specificity. The use of PNA instead of DNA as probes 16 provides additional benefits because PNA has no inherent charge as does DNA. This will be explained below. It is noted, however, that the scope of the invention is not limited to sensing the hybridization of a DNA molecule to PNA or DNA molecular receptors 16. For example, embodiments of the present invention can also be utilized to detect RNA hybridization.

The identification or analysis process includes providing a solution 20 containing target molecules 22, a plurality of oligonucleotide segments 23 and ligase. The sequence of probes 16 together with the sequence of oligonucleotide segments 23 complement the sequence of the target molecules being tested for. Each oligonucleotide segment 23 is tagged by a marker 24 which function as a signal for identification. Typically, optical detection methods are employed to detect the signal (marker).

Target molecules 22 are typically in such a low concentration that conventional techniques are unable to detect the signal from very low number of hybridization events. Furthermore, the low concentration of target molecules 22 also reduces the likelihood of hybridization. By charging electrode 14 and electrode 15, an electric field can be generated surrounding oligonucleotide probes 16. If the polarity is correct, namely electrode 14 being positive and electrode 15 being negative when target molecules 22 are DNA strands, target molecules 22 are attracted to oligonucleotide probes 16. Thus the concentration of target molecules 22 increases proximate probes 16 thereby increasing the probability of hybridization.

When hybridization occurs oligonucleotide segments 23 also hybridize with target molecules 22. When this occurs, probes 16 and segments 23 are joined by a covalent bond 25 due to the presence of ligase in solution 20.

Figure 2:
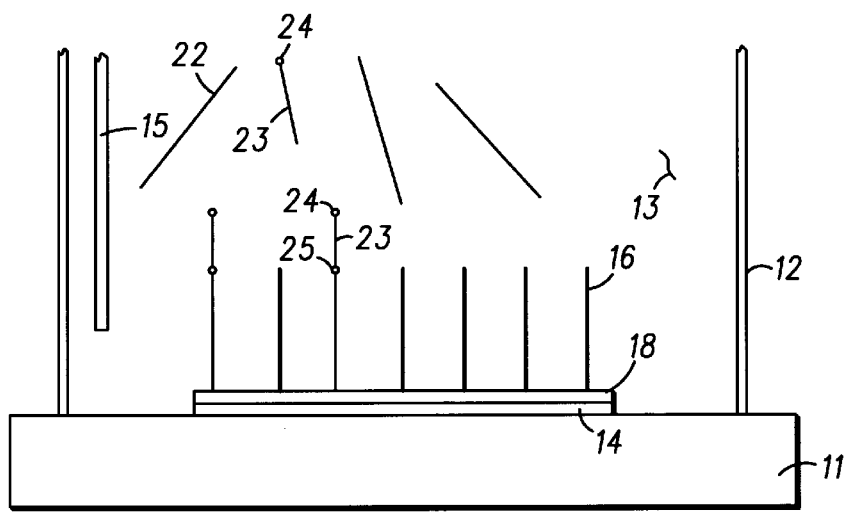
FIG. 2 is a simplified sectional view similar to FIG. 1 as the molecular detection apparatus would appear during strand separation.

Referring now to FIG. 2, after hybridization occurs, target molecules 22 are separated from oligonucleotide probes 16 and oligonucleotide segments 23 by reversing the polarity of the electric field. Since target molecules 22 are coupled to probes 16 and segments 23 by a hydrogen bond, which is weaker than a covalent bond, target molecules 22 can be separated from probes 16 and segments 23 without breaking the covalent bond coupling probes 16 and segments 23 together. An electric field is generated surrounding oligonucleotide probes 16, with electrode 14 being negative and electrode 15 being positive. It will be understood that this continues the example of target molecules 22 being DNA molecules which have an inherent negative charge. After separation occurs, target molecules are again free in solution 20 along with additional oligonucleotide segments 23.

At this point, some probes 16 have oligonucleotide segments 23 covalently bonded thereto. Markers 24 now attached to probes 16 signal a hybridization event. Signal gain is amplified by again reversing the polarity of electrodes 14 and 15, generating an electric field generally the same as initially generated surrounding probes 16 to attract target molecule 22 to the remaining unmarked probes 16. Hybridization occurs between some of the remaining probes 16 and target molecules 22, whereupon some of the additional oligonucleotide segments 23 hybridize with target molecules 22. Segments 23 are joined by covalent bond to the hybridized probes 16 due to the presence of ligase in solution 20.

After each cycle, additional markers 24 are attached to probes 16, increasing the signal gain. Large numbers of cycles can occur in a very short period of time by pulsing between the opposing electric fields. What would takes hours by using thermal techniques can be accomplished in seconds or minutes. Furthermore, because temperature is maintained at optimal levels for hybridization, heat sensitive ligase as well as heat resistant ligase can be used.

After a sufficient number of cycles to adequately amplify the signal, solution 20 is removed from volume 13 surrounding probes 16. Markers 24 attached to oligonucleotide segments 23 covalently bonded to oligonucleotide probes 16 are then detected using any desired conventional method.

Probes 16 are preferably PNA molecules because of their lack of an inherent electric charge. Typically, a DNA target molecule is repelled from a DNA probe because they each have a negative charge. This can be overcome by increasing the ionic strength of a solution to mask the inherent charge of DNA. Because PNA lack a charge, the DNA target molecules will not be repelled. Thus the ionic strength of solution 20 need not be high.

Figure 3:
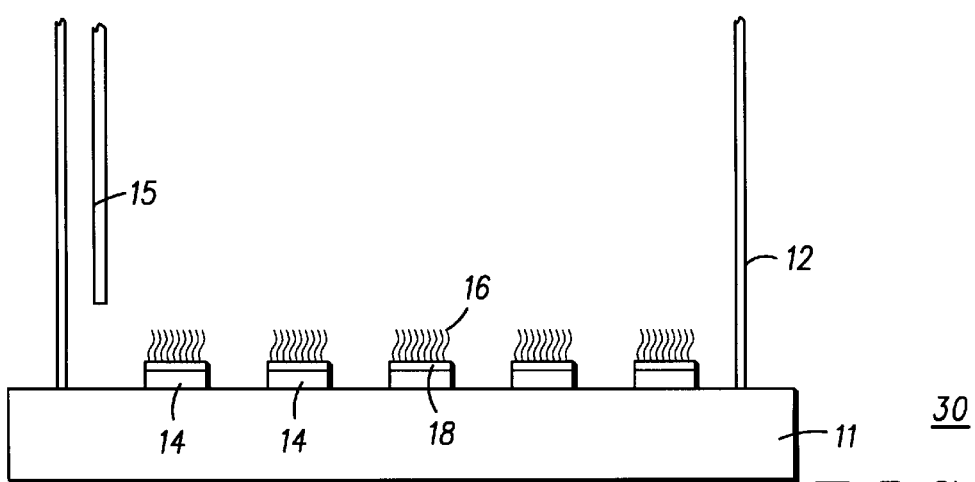
FIG. 3 a simplified sectional side view of an array of the molecular detection apparatus of FIGS. 1 and 2.

Turning now to FIG. 3, a side view of a molecular detection apparatus 30 including an array of electrodes 14 carried by support 11, and defining a plurality of binding sites is illustrated. Each binding site is the same as described above in connection with FIGS. 1 and 2. Molecular receptors (probes) 16 on respective electrodes 14 differ in base sequence for simultaneous detection of a plurality of different target molecules within a single array. Preferably, the analysis using an array includes repeating the steps of described above in connection with FIGS. 1 and 2. An electric field is generated at one of electrodes 14, although it will be understood that more than one of electrodes 14 can be included. The polarity of the electric field is reversed a plurality of times at a specific binding site defined by the electrode The steps of generating and alternating the polarity of an electric field is sequentially repeated a plurality of times at each of the plurality of binding sites by sequentially charging electrodes 14. Target molecules 22 repeatedly hybridize to a portion of probes 16, which it compliments, while concurrently, oligonucleotide segments 23 hybridize with target molecules 22 at each hybridized probe 16. Upon removing the solution, target molecules 22 can be identified by detecting which binding site has markers 24 attached to oligonucleotide segments 23 covalently bonded to probes 16.

Thus provides is a new and improved method and apparatus for identifying molecules employing ligase analysis having greatly reduced cycle time and without requiring heat resistant ligase.

Various modifications and changes to the embodiments herein chosen for purposes of illustration will readily occur to those skilled in the art. Other modifications and variations may be made by those skilled in the art without departing from the scope of the invention as defined by the following claims.

Having fully described and disclosed the present invention and preferred embodiment thereof in such clear and concise terms as to enable those skilled in the art to understand and practice same, the invention claimed is:

1. An electric field amplified oligonucleotide ligase analysis comprising the steps of:

providing an electrode having a plurality of oligonucleotide probes covalenty bound thereto;

providing a solution including ligase and a plurality of individual oligonucleotide segments each including a marker, the electrode being positioned in the solution;

introducing a target molecule into the solution;

using the electrode, generating a first electric field surrounding the plurality of oligonucleotide probes to attract the target molecule to a first of the plurality of oligonucleotide probes to which it hybridizes, whereupon a first of the plurality of oligonucleotide segments hybridizes with the target molecule and covalently bonds to the first oligonucleotide probe due to the presence of ligase in the solution;

separating the target molecule from the first oligonucleotide probe and the first oligonucleotide segment by generating, using the electrode, a second electric field oppositely polarized to the first electric field and surrounding the plurality of oligonucleotide probes;

repeatedly cycling the generating and separating steps by pulsing between the first and the second electric fields to covalently bond a plurality of the plurality of individual oligonucleotide segments to the plurality of oligonucleotide probes; and performing an oligonucleotide ligase analysis by detecting the markers included with oligonucleotide segments covalently bonded with oligonucleotide probes.

2. A method as claimed in claim 1 wherein the oligonucleotide probe is selected from the group consisting of a peptide nucleic acid and a deoxyribonucleic acid.

3. A method as claimed in claim 2 wherein the oligonucleotide probe includes a chain of at least one nucleotide, and wherein the target molecule includes a complementary chain of at least one nucleotide.

4. A method as claimed in claim 3 wherein the target molecule is selected from the group consisting of a DNA molecule and an RNA molecule.

5. A method as claimed in claim 1 wherein the step of providing the electrode includes the electrode having a plurality of identical oligonucleotide probes covalently bonded thereto.

6. A method as claimed in claim 5 wherein an array of electrodes is provided, and wherein each electrode has a plurality of identical oligonucleotide probes covalently bonded thereto, and wherein the nucleotide sequence of the probes at each electrode differs from the nucleotide sequence at every other electrode.

7. A method as claimed in claim 1 wherein the steps of generating and separating include providing a counter electrode in the solution, spaced from the electrode having a plurality of oligonucleotide probes covalently bound thereto.

8. An electric field amplified oligonucleotide ligase analysis comprising the steps of:

providing an array of electrodes, wherein each electrode has a plurality of identical oligonucleotide probes covalently bonded thereto, and wherein the nucleotide sequence of the probes at each electrode differs from the nucleotide sequence of the probes at every other electrode;

providing a solution including ligase and a plurality of individual oligonucleotide segments each including a marker;

introducing a plurality of target molecules into the solution;

generating a first electric field surrounding the plurality of oligonucleotide probes at a first of the electrodes to attract a first target molecule to the first of the electrodes;

generating a second electric field surrounding the plurality of oligonucleotide probes at the first electrode to force the first target molecule from the first electrode and oligonucleotide probes thereon;

repeating the steps of generating the first and the second electric fields a plurality of times at the first electrode;

sequentially repeating the steps of generating the first and the second electric fields a plurality of times at each of the plurality of electrodes, wherein a complementary target molecule of the plurality of target molecules repeatedly hybridizes to complementary oligonucleotide probes of the plurality of oligonucleotide probes and wherein oligonucleotide segments concurrently hybridize with the complementary target molecule at each hybridized oligonucleotide probe and are covalently bonded to the oligonucleotide probe due to the presence of ligase in the solution;

removing the solution; and performing an oligonucleotide ligase analysis by detecting the markers attached to the oligonucleotide segments covalently bonded to the oligonucleotide probes at each electrode of the array of electrodes.

* * * * *